United States Patent [19]

Kennedy et al.

[11] 4,210,737

[45] Jul. 1, 1980

[54] SYNTHESIS OF SUBSTITUTED CYCLOPENTADIENES AND CYCLOPENTADIENE-FUNCTIONALIZED POLYMERS

[76] Inventors: Joseph P. Kennedy, 952 Genesee Rd., Akron, Ohio 44303; Kenneth F. Castner, 2365 Cooledge Ave., Akron, Ohio 44305

[21] Appl. No.: 962,048

[22] Filed: Nov. 20, 1978

Related U.S. Application Data

[62] Division of Ser. No. 770,436, Feb. 22, 1977, Pat. No. 4,138,441.

[51] Int. Cl.$^2$ .................. C08F 4/52; C08F 210/10
[52] U.S. Cl. .................. 526/185; 260/3.3; 525/274; 526/348.6
[58] Field of Search .................. 526/185

[56] References Cited

U.S. PATENT DOCUMENTS

| | | | |
|---|---|---|---|
| 2,953,607 | 9/1960 | Hafner | 260/666 A |
| 3,376,331 | 4/1968 | Kroll | 526/185 |
| 3,489,691 | 1/1970 | Meckler et al. | 526/185 |
| 3,560,458 | 2/1971 | Kennedy et al. | 526/185 |
| 4,138,441 | 2/1979 | Kennedy et al. | 526/185 |

FOREIGN PATENT DOCUMENTS

1163339  9/1969  United Kingdom .................. 526/185

*Primary Examiner*—William F. Hamrock
*Attorney, Agent, or Firm*—John Y. Clowney

[57] ABSTRACT

Aluminum cyclopentadienyl compounds can be used to synthesize a variety of organic molecules containing the cyclopentadiene group, e.g., substituted cyclopentadiene compounds, polymer molecules with cyclopentadiene pendant groups, and polymer molecules with cyclopentadiene terminal groups.

4 Claims, No Drawings

SYNTHESIS OF SUBSTITUTED CYCLOPENTADIENES AND CYCLOPENTADIENE-FUNCTIONALIZED POLYMERS

This is a divisional application of Ser. No. 770,436, filed Feb. 22, 1977, now U.S. Pat. No. 4,138,441.

This invention relates to the use of novel aluminum hydrocarbon compounds in the synthesis of substituted cyclopentadienes and polymers containing pendant cyclopentadienyl groups and polymers containing a terminal cyclopentadienyl group.

BACKGROUND OF THE INVENTION

It is known that certain hydrocarbon halides such as alkyl halides in combination with organoaluminum compounds initiate the polymerization of cationically polymerizable monomers, such as isobutylene, styrene, α-methylstyrene, etc. (see for example, U.S. Pat. No. 3,694,377). It is also known that the hydrocarbon halide need not be a small molecule, but may be part of a polymer chain, such as exists in chlorobutyl rubber, chlorinated ethylene-propylene copolymer, PVC, neoprene, etc. (see for example, U.S. Pat. No. 3,904,708).

Comprehensive studies of hydrocarbon halide (initiator)/hydrocarbon-aluminum (coinitiator) initiator systems have led to an increased understanding of the initiation process (see J. P. Kennedy, J. Org. Chem., Vol. 35 p. 532, 1970). The major conclusion drawn from these studies is that the aluminum compound interacts with the hydrocarbon halide to ionize the carbon-halogen bond. The carbenium ion thus generated initiates the polymerization process. The reaction is viewed as proceeding by the following scheme:

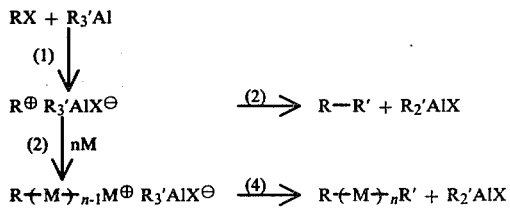

Thus the organohalide (RX) reacts with an alkylaluminum compound ($R_3'Al$) to ionize the carbon-halogen bond in the initiator (eq. 1). In the absence of monomer (M), the ioncounterion complex collapses via reaction of $R\oplus$ with an anion ($R'\ominus$) from the counterion. However, if monomer is present, cationic polymerization ensues and generates a macromolecular-carbenium ion/counterion complex (eq. 3). Subsequently, this complex collapses via alkylation as in eq. 2 to yield a polymer with R' terminal group (eq. 4).

Knowledge gained from model studies has been exploited in the synthesis of: (1) quarternary-carbon containing compounds via reaction of tertiary hydrocarbon halides with $R_3Al$ (see J. P. Kennedy, J. Org. Chem., Vol. 35 p. 532, 1970); (2) graft and bigraft copolymers via utilization of activechlorine-containing polymers as initiators (see J. P. Kennedy and R. R. Smith, Recent Advances in Polymer Blends, Grafts and Blocks, ed. L. H. Sperling, Plenum Press, New York, 1974, pp. 303–357), and (3) block copolymers via utilization of difunctional initiators (see J. P. Kennedy and E. Melby, J. Macromol. Sci., Chem. A9(5) p. 833, 1975). It can thus be seen that exploitation of the hydrocarbon halide/hydrocarbon aluminum reactions has been primarily directed towards a controlled initiation in carbenium ion polymerizations, and subsequently placing well defined head groups in polyolefin chains.

Although the model studies also provided an understanding of termination mechanisms, and showed that termination involved reaction of the carbenium ion with an anion from the alkyl-aluminum counterion, utilization of the alkylative termination was greatly limited due to the unreactive saturated hydrocarbon groups formed. Outside of synthesis of quarternary carbon containing compounds, utilization of alkylative termination has been confined to alkylating active chlorine sites (tertiary or allylic) on PVC. Thus PVC was treated with $R_3Al$ compounds to alkylate the active sites, giving the stronger carbon-carbon bonds. It was speculated, and later verified, that such treatment on PVC would enhance its thermal stability (see J. P. Kennedy and M. Ichikawa, Poly. Eng. and Sci., 14, p. 322, 1974).

Therefore, the utilization of alkyl halide or hydrocarbon halide/alkylaluminum or hydrocarbon aluminum reactions to generate organic compounds with versatile functional groups has been ignored.

The novelty of this invention is a generalized process to synthesize cyclopentadiene-functionalized molecules, and primarily, cyclopentadiene-functionalized polymers, via Lewis acid chemistry. The scope of functionalized polymers prepared by the processes of this invention include polymers with cyclopentadiene pendant groups and polymers with cyclopentadiene terminal groups.

The prior art in the synthesis of polymers with pendant cyclopentadiene groups involved either copolymerizations with allyl-dicyclopentadiene compounds, with subsequent thermal cracking of the dicyclopentadiene pendant groups, or by reaction of alkali metal salts of cyclopentadiene with halogenomethylated polyethers (see U.S. Pat. No. 3,826,760). These processes are limited by the problems inherent in copolymerizations, e.g., blockiness, and the general detrimental effect bases have on chlorine-containing polymers.

The prior art in the synthesis of cyclopentadiene-end group polymers involves the capping of living anionic polymerization chains with fulvenes, subsequent reaction with an alcohol yielding polymers with cyclopentadiene terminus (see Japanese Pat. No. 100,492/73). The reaction was viewed as occurring by the following scheme, illustrated with butadiene monomer:

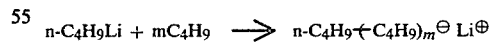

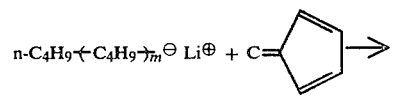

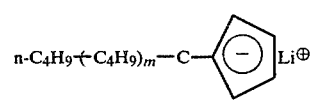

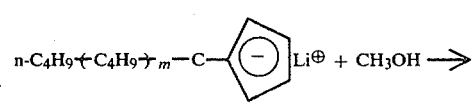

-continued

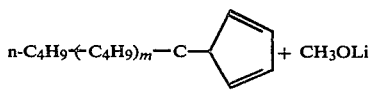

This process is limited to monomers which will polymerize anionically e.g., conjugated dienes, styrene and its derivatives.

SUMMARY OF INVENTION

It has been found that aluminum cyclopentadiene or aluminum cyclopentadienyl compounds $R_x'Al(CPD)_y$, as hereinafter defined, can be used as cyclopentadienylating agents in reactions with certain hydrocarbon halides. More specifically, $R_x'Al(CPD)_y$ reacts with active-halogen-containing compounds, such as tertiary, allylic or benzylic halides, resulting in the replacement of the chlorine with a cyclopentadiene group. The active halogen may be attached to a small molecule, such as tertiary-butyl chloride or allyl chloride, or attached to a polymer such as chlorobutyl rubber, chlorinated ethylenepropylene copolymer or neoprene, which contains small amounts of tertiary -allylic chlorines. It has also been discovered that cationic polymerizations initiated with $RCl/R_x'Al(CPD)_y$ systems terminate via alkylation of the polymeric carbenium ion with a CPD group from the alkylaluminum halide counterion.

In brief, the process of this invention involves the mixing of certain hydrocarbon halides or active-halogen-containing polymers with $R_x'AlCPD_y$ and in some cases with a cationically polymerizable monomer for polymerizations in bulk or in an inert solvent in the temperature range from about −80° C. to +50° C. for periods sufficient to effect the desired conversions.

DETAILED DESCRIPTION OF INVENTION

In particular this invention relates to the use of aluminum cyclopentadienyl compounds in conjunction with suitable organo halides in the synthesis of: (1) substituted cyclopentadienes and (2) polymers containing cyclopentadiene pendant groups. This invention is further directed towards the employment of hydrocarbon halide/aluminum cyclopentadienyl compound $R_x'Al(CPD)_y$ initiator/coinitiator systems for the synthesis of cylopentadiene-terminal group polymers.

Still more particularly, this invention relates to the synthesis of substituted cyclopentadienes by reaction of tertiary, allylic or benzylic halides with $R_x'Al(CPD)_y$ compounds;

This invention also relates to the modification of active-halogen-containing polymers, substituting a cyclopentadiene group for the halogen atom, i.e.,

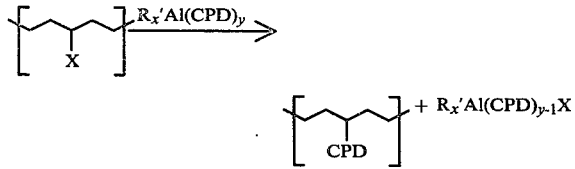

These polymer modification reactions offer a unique and novel way of attaching a very versatile group, the cyclopentadiene group, to relatively non-functional group polymers. The pendant cyclopentadiene groups can undergo a variety of subsequent useful reactions, e.g., Diels-Alder condensations, including dimerization of the cyclopentadiene pendant group, yielding thermally reversible crosslinks via Diels-Alder/retro-Diels-Alder reactions.

This invention is further directed to the synthesis of polymers with cyclopentadiene end groups. Thus, a process of this invention can be employed for the synthesis of reactive end-group polymers via polymerization of cationically polymerizable monomers initiated with hydrocarbon halide/$R_x'Al(CPD)_y$ initiator systems.

The processes of this invention involve the mixing of suitable hydrocarbon halides with aluminum cyclopentadienyl compounds in the presence of monomer for polymerizations in inert solvents in the temperature range of −80° to +50° C.

Suitable hydrocarbon halides (RX) are those defined as tertiary, allylic or benzylic. More precisely, suitable alkyl halides are those in which the halogens are on tertiary, allylic or benzylic carbon atoms. The halogen (X) may be either chlorine, bromine or iodine.

Representative, but not exhaustive, of suitable hydrocarbon halides are: tertiary butyl bromide, tertiary butyl chloride, tri-n-butyl chloromethane, allyl chloride, methallyl chloride, crotyl chloride, 1-chloro-butene-2, 2,6-dichloro-2,6-dimethylheptane, 2-chloro-6-bromo-2,6-dimethylheptane, benzyl chloride, benzyl bromide, methylphenyl chloromethane, triphenyl chloromethane, and the like.

By aluminum cyclopentadienyl compounds is meant compounds of the type $R_x'Al(CPD)_y$, where CPD represents the cyclopentadine group, $R'$ represents an alkyl, cycloalkyl, alkenyl, cycloalkenyl or aromatic group, y equals one to two, and x equals two to one, the sum of x and y being equal to three.

Representative, but not exhaustive, of suitable coinitiators are: diisobutylaluminum cyclopentadiene or diisobutyl(cyclopentadienyl)aluminum, diethylaluminum cyclopentadiene or diethyl(cyclopentadienyl)aluminum, dimethylaluminum cyclopentadiene or dimethyl(cyclopentadienyl)aluminum, methylaluminum-bis-cyclopentadiene or methyl(bis-cyclopentadienyl)aluminum and aluminum-tris-cyclopentadiene or tris-cyclopentadienyl aluminum.

The preferred organoaluminums of the present invention are $R_2'AlCPD$ compounds, and the most preferred is dimethylaluminum cyclopentadine or dimethyl(cyclopentadienyl)aluminum.

Suitable solvents for $RX+R_x'Al(CPD)_y$ reactions are those which will not deactivate the aluminum compound. Representative, but not exhaustive, of such solvents are aliphatic hydrocarbons, e.g., pentane, hexane, cyclohexane, or chlorinated hydrocarbons, e.g. methyl chloride, ethyl chloride, dichloromethane, 1,2-dichloroethane, chlorobenzene, o-chlorotoluene, and the like.

The ractions can be conveniently carried out in the +50° to −80° C. range, however, the preferred range is +25° to −70° C. and most preferably 0° to −50° C.

The synthesis of substituted cyclopentadienes is carried out by mixing RX with $R_x'Al(CPD)_y$ preferably in an inert solvent. The addition order of the components is not critical, however, it is preferred to add RX, as a dilute solution or neat, to a $R_x'Al(CPD)_y$ solution. Although the molar ratio of RX to $R_x'Al(CPD)_y$ (X/Al) is not critical, it is preferred to employ X/Al ratios in the range of 0.10 to 1.0. Staying within this molar ratio minimizes the formation of $RAlX_2$ compounds, which are thought to lead to detrimental side reactions.

The temperature at which the reactions are carried out is within the $+50°$ to $-80°$ C. range, preferably $+20°$ to $-65°$ C. and most preferably $0°$ to $-55°$ C.

The reactions of alkyl halides with $R_x'Al(CPD)_y$ compounds is viewed as occurring by the following scheme, invoking a carbenium ion/counterion transitory complex.

$$RX + R_x'Al(CPD)_y$$
$$\downarrow$$
$$R^{\oplus}R_x'Al(CPD)_yX^{\ominus}$$
$$\downarrow$$
$$R-CPD + R_x'Al(CPD)_{y-1}X$$

The substituted cyclopentadiene product can consist of several isomeric products based on the point of attachment of the alkyl group to the cyclopentadiene ring. The isomers being 1,2 or 5-alkyl cyclopentadiene, illustrated below

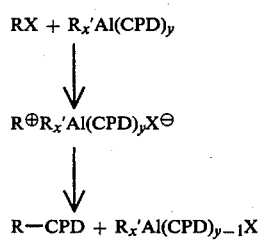

| 1-alkylcyclo- | 2-alkylcyclo- | 5-alkylcyclo- |
| pentadiene | pentadiene | pentadiene |

However, the isomeric product is not critical to the present invention.

The synthesis of polymers with cyclopentadiene pendant groups is similar to that employed for the synthesis of substituted cyclopentadienes. However, the alkyl halide in this process is a polymer containing many active-halogen sites. Again, by active halogen is meant halogens attached to tertiary, allylic or benzylic carbon atoms. Suitable polymers which can be cyclopentadiene-functionalized by treatment with $R_x'Al(CPD)_y$ compounds include: polyvinylchloride, polyvinylidene chloride, polyvinylbromide, polychloroprene and the like. Still other suitable examples are polymers which have been modified by post-polymerization treatment to introduce active halogens onto the polymer backbone include: chlorobutyl rubber, brominatedbutyl rubber, chlorinated ethylenepropylene (Cl-EPR) copolymer, chlorinated natural rubber, chlorinated ethylene-propylene-diene (Cl-EPDM), chlorinated polyethylene and the like.

It is noted that some of the above polymers are not generally thought of as containing tertiary, allylic or benzylic halogens, however, such groups are frequently introduced into the polymer by an irregular addition step, e.g., small amounts of 1,2 addition of chloroprene, in an otherwise essentially 1,4 polymerization, results in polychloroprene containing small amounts of tertiary-allylic chlorines.

The $R_x'Al(CPD)_y$ modification of active-halogen-containing polymers to yield polymers with cyclopentadiene pendant groups is carried out by mixing the subject polymer with $R_x'Al(CPD)_y$ in an inert solvent. Suitable solvents are the same as described earlier for the synthesis of substituted cyclopentadienes, however, the solvent now has the added qualification that it must be a good solvent for the polymer also. Although the addition order of components is not critical, it is more convenient to add a $R_x'Al(CPD)_y$ solution to the polymer solution.

The preferred $R_x'Al(CPD)_y$ to polymer weight ratio is dependent upon the polymer employed and thus on the amount of polymer-bound-active halogens, temperature and desired reaction time. However, the best $R_x'Al(CPD)_y$ to polymer weight ratio can readily be determined by one skilled in the art.

As in the synthesis of substituted cyclopentadienes, the polymer modification reactions are run in the $+50°$ to $-80°$ C. range. However, the preferred range is $+35°$ to $-65°$ C., and more preferably $+20°$ to $-55°$ C.

The cyclopentadienylation of active-halogen-containing polymers with $R_x'Al(CPD)_y$ is viewed as occurring by the following scheme

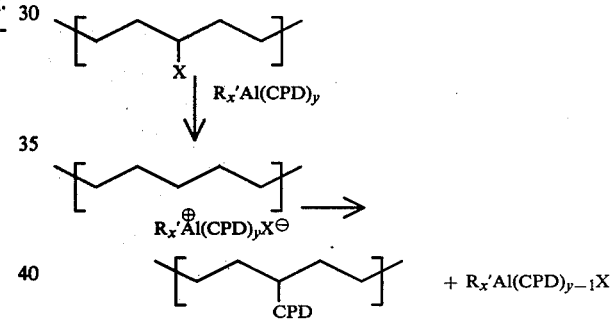

Due to the great propensity for the pendant cyclopentadienes to undergo Diels-Alder dimerization, yielding a cross-link polymer, i.e.,

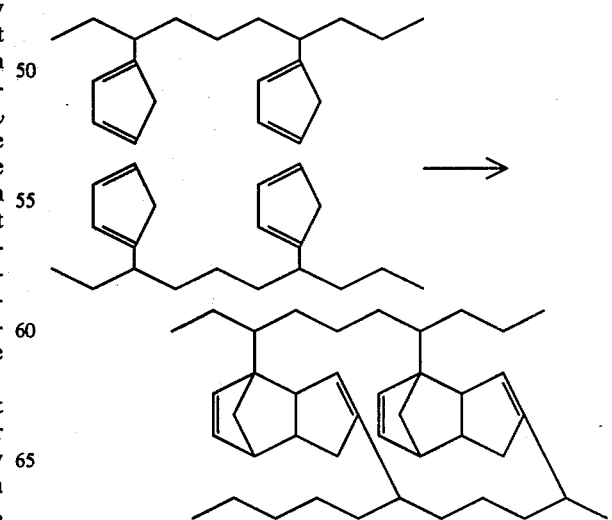

the derivatized polymers should be stored at low temperatures. However, it has been found the crosslinks so obtained can be broken by heating to >150° C., i.e., thermally reversible crosslink, (this work and U.S. Pat. No. 3,826,760). Also, the cyclopentadiene groups can be capped, thus preventing gelation, by reaction with other dienophiles, e.g. maleic anhydride. Indeed, the reaction of the cyclopentadiene groups with polar dienophiles offer a simple route to attaching polar groups to the cyclopentadienylated polymers.

The synthesis of polymers with cyclopentadiene terminal groups is carried out by mixing a suitable alkyl halide (RX), $R_x'Al(CPD)_y$ and a cationically polymerizable monomer in an inert solvent. The preferred order is to add $R_x'Al(CPD)_y$ to the monomer (bulk or in solution), followed by RX under vigorous mixing.

$R_x'Al(CPD)_y$, RX and inert solvents are the same as described earlier. Suitable monomers are those classified as cationically polymerizable. Representative, but not exhaustive, of such monomers are: isobutylene, styrene and its derivatives, methylene nobornene, cyclopentadiene, dimethyl butadiene, and piperylene.

It is to be noted that the above list of monomers includes cyclopentadiene. It may therefore appear that the cyclopentadiene end group would be consumed by cationic polymerization. And indeed, in all the various cyclopentadiene-functionalized molecules described in this invention, it would be expected that cationic reactions would consume a large portion of the functional group. However, detailed studies have shown that the kinetic product of the cyclopentadienylations described herein is the 5-substituted cyclopentadiene (J. P. Kennedy and K. F. Castner, Polymer Preprints, in press), which under the conditions employed in this invention is not consumed via side reactions.

The polymerizations can be carried out in the +50° to −100° C. range, however, the preferred range is 0 to −90, and the most preferred range is −30° to −80° C.

One of the specific embodiments of this invention is the method of preparing polymers containing pendant cyclopentadiene groups which comprises reacting a polymer containing pendant active-halogens selected from the group consisting of chlorine, bromine and iodine with an aluminum cyclopentadienyl compound of the formula $R_x'Al(CPD)_y$ wherein CPD represents the cyclopentadiene group, R' represents an alkyl, cycloalkyl, alkenyl, cycloalkenyl, alkaryl or aryl group, y equals 1 to 2 and x equals 2 to 1 and the sum of x plus y is equal to 3.

Another of the embodiments of this invention is a method of preparation of hydrocarbon-substituted cyclopentadienes which comprises reacting a compound of the formula $R_x'Al(CPD)_y$ wherein CPD represents the cyclopentadienyl group, R' represents an alkyl, cycloalkyl, alkenyl, cycloalkenyl, alkaryl or aryl group, y equals 1 to 2 and x equals 2 to 1 and the sum of x plus y is equal to 3, with a tertiary, allylic or benzylic halide of the formula RX, wherein R is selected from the group consisting of alkyl, cycloalkyl, alkenyl, cycloalkenyl, alkaryl or aryl, and X represents chlorine, bromine or iodine.

Another embodiment of the present invention is a method for preparing a polymer containing a cyclopentadiene terminal group which comprises reacting a material selected from the group consisting of isobutylene, styrene and α-methylstyrene with an initiator consisting of tertiary, allylic or benzylic halide of the formula RX, wherein R is selected from the group consisting of alkyl, cycloalkyl, alkenyl, cycloalkenyl, alkaryl or aryl, and X represents chlorine, bromine or iodine, and $R_x'Al(CPD)_y$ wherein CPD represents the cyclopentadiene group, R' represents an alkyl, cycloalkyl, alkenyl, cycloalkenyl, alkaryl or aryl group, y equals 1 to 2 and x equals 2 to 1 and the sum of x plus y is equal to 3.

When isobutylene, styrene and/or α-methylstyrene is polymerized, the mole ratio of $RX/R_x'Al(CPD)_y$ may range from 0.1/1 to 5.0/1.

This invention is further illustrated by the following examples. For these examples all reactions were run in a stainless steel drybox under a dry nitrogen atmosphere. The products obtained in the synthesis of substituted cyclopentadienes were identified by gas chromatography employing peak enhancement with authentic samples. Polymer pendant or terminal cyclopentadiene groups were detected and quantitatively measured by UV spectroscopy, and further verified by reactions on the cyclopentadiene group.

EXAMPLE 1

Synthesis of tertiary-butyl cyclopentadiene

In runs 1 through 10, five ml. of 0.025 M dimethylaluminum cyclopentadiene ($Me_2AlCPD$) in chlorobenzene was dispensed by pipette into 20×150 mm test tubes. The tubes were then capped with screw caps fitted with self-sealing gaskets and Teflon ® liners. The reaction tubes were placed in a constant temperature bath. After allowing sufficient time for the tubes and contents to attain bath temperature, 0.12 M tert.-butyl chloride solution in chlorobenzene (tBuCl) already at bath temperature was added by syringe fitted with hypodermic needle. After the desired time, the reactions were quenched by the addition of normal-butyl alcohol.

The amounts of t-butyl chloride, the mole ratio of t-BuCl to $Me_2AlCPD$, the time of reaction, the temperature employed and the yield of t-butylcyclopentadiene (t-BuCPD) in mole percent is reported in Table 1 below.

Table I

| Run | tBuCl (ml. 0.12M) | [t-BuCl] [Me$_2$AlCPD] | Time [Min] | Temp. [°C.] | t-BuCPD Yield (mole %) |
|---|---|---|---|---|---|
| 1 | 0.25 | 0.24 | 30 | +1 | 60 |
| 2 | 0.50 | 0.48 | " | " | 63 |
| 3 | 0.75 | 0.73 | " | " | 70 |
| 4 | 0.90 | 0.87 | " | " | 66 |
| 5 | 1.10 | 1.06 | " | " | 24 |
| 6 | 0.50 | 0.48 | 60 | +23 | 50 |
| 7 | " | " | " | +1 | 63 |
| 8 | " | " | " | −9 | 75 |
| 9 | " | " | " | −19 | 72 |
| 10 | " | " | " | −29 | 84 |

The results from runs 1 through 5 indicate little effect of the tBuCl/Me$_2$AlCPD mole ratio on the yield of tertiary-butylcyclopentadiene (tBuCPD) for ratios less than ~0.90. However, at tBuCl/Me$_2$AlCPD greater than ~0.90 the yield decreases considerably. Runs 6 through 10 show the effect of temperature on tBuCPD yield. The increasing tBuCPD yield with decreasing temperature indicates that lower temperatures increase the cyclopentadienylation to methylation ratio, i.e.,

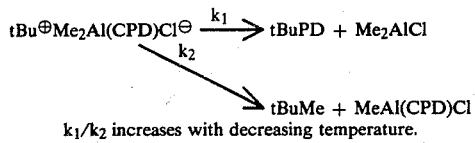

$k_1/k_2$ increases with decreasing temperature.

EXAMPLE 2

Cyclopentadienylation of Chlorobutyl Rubber

A commercial chlorobutyl rubber of $\overline{M}_n$ 200,000 and containing 1.1 wt % chlorine was purified by three reprecipatations from benzene by adding methanol to 5% (wt/vol) polymer solutions. The coagulated polymer was vacuum dried at 50° C. for 72 hr.

5.0 g of the purified polymer was dissolved in 250 ml of dried chlorobenzene. The reaction vessel was placed into a −23° C. bath. After allowing sufficient time for the polymer solution to attain bath temperature 2.84 millimole of $Me_2AlCPD$ was added as a 0.025 M solution in chlorobenzene. After 60 min 2 ml. of methanol was added to the solution to quench the reaction without effecting coagulation of the polymer. A 25 ml aliquot of the polymer solution was removed by pipette and coagulated with methanol. The rest of the polymer solution was filtered to remove insoluble aluminum residues, then coagulated with a 1% 2,6-ditertiary butyl-p-cresol solution in methanol and vacuum dried at 22° C. for 72 hr.

The cresol-free polymer was reprecipitated 3 times from spectro grade n-hexane by coagulation with methanol and rapidly dried at 22° under high vacuum. UV analysis on dilute polymer solution in n-hexane showed the polymer to contain 1.1% (wt) cyclopentadiene. This result indicates that 55% of the chlorine sites were cyclopentadienylated.

An aliquot (0.25 g) of the 2,6-ditertiary-butyl-p-cresol-treated polymer was dissolved in 25 ml of chlorobenzene and 0.25 g of maleic anhydride was added. After 1 hr at room temperature (to ensure complete dissolution of polymer and anhydride) the solvent was heated to reflux for ~1 hr. The reaction solution was cooled to room temperature and the polymer coagulated by the addition of methanol. The polymer was purified by three reprecipitations from spectro grade carbon tetrachloride ($CCl_4$) and vacuum dried. Anhydride content of the polymer was determined by IR analysis in a dilute polymer solution in $CCl_4$, and was found to be 1.6% (wt), which corresponds to 1.1% cyclopentadiene.

A portion of the cyclopentadienylated polymer (totally soluble) was heated in a curing press at 150° C. for ~30 min. After this treatment the polymer was found to be insoluble. It was believed that the crosslinks were due to the Diels-Alder dimerization of the pendant cyclopentadiene groups. To verify this, the polymer was reheated at 170° to effect the retro-Diels-Alder reaction. Although the polymer flowed in the mold cavity it was still insoluble. It therefore appeared that the polymer could flow at high temperatures, where the dimer would crack, however, upon cooling the dimer reformed. To substantiate this concept, the crosslinked polymer was heated to 200° C. in hexachlorobutadiene containing maleic anhydride. Therefore, it was visualized that the pendant cyclopentadiene monomer would react with maleic anhydride giving a norbornene dicarboxylic anhydride pendant group, and thus have capped the cyclopentadiene group. The polymer thus treated, was solubilized and IR analysis showed the presence of the anhydride group.

EXAMPLE 3

Cyclopentadienylation of Chlorinated Ethylene-Propylene Copolymer

Using a well known technique a commercial ethylene-propylene rubber (EPR) was chlorinated. The EPR was dissolved in benzene and chlorine gas was bubbled through the solution while the mixture was treated with ultra violet light.

The modification of chlorinated ethylene-propylene copolymer (Cl-EPR) was carried in the same manner as that employed for Cl-IIR. The Cl-EPR was of $\overline{M}_n$ 65,000 and contained 3.0% (wt) chlorine. However, only a small portion of these chlorines are thought to be active towards alkylaluminum compounds, as a result of the free radical chlorination process employed.

The procedure was to dissolve 8.7 g of Cl-EPR in 250 ml of chlorobenzene and then add 2.5 millimole of dimethylaluminum cyclopentadiene or dimethyl(cyclopentadienyl)aluminum. The conditions and results are reported in Table II below.

Table II

| Run | Cl/Al* | Temp. (°C.) | Reaction Time (min) | Cyclopentadiene Content (wt %) | Cl sites substituted with CPD (wt %) |
|---|---|---|---|---|---|
| 1 | 2.9 | −23 | 60 | 0.31 | 6 |
| 2 | 1.8 | −13 | " | 0.91 | 17 |
| 3 | 0.55 | −13 | " | 1.3 | 23 |

*chlorine to $Me_2AlCPD$ mole ratio

The $Me_2AlCPD$-treated polymer in Run 1 has 0.31% (wt) cyclopentadiene. Subsequent reaction with maleic anhydride yielded a polymer containing 0.47% (wt) anhydride, which corresponds to 0.31% cyclopentadiene. The low cyclopentadiene content for Run 1 probably indicates incomplete reaction. The thermally reversible crosslinks observed with cyclopentadienylated Cl-IIR were also operative in cyclopentadienylated Cl-EPR.

EXAMPLE 4

Synthesis of Polyisobutylene with Cyclopentadiene End-Group

Polyisobutylene polymerizations were carried out in test tubes employing the same technique as described for the synthesis of tBuCPD in Example 1 except that isobutylene is included in the recipe.

In a typical polymerization, purified isobutylene (and n-pentane in some cases) was added to cooled chlorobenzene solvent

Table III

| Run | Isobutylene (ml) | n-pentane (ml) | Chlorobenzene (ml) | Temp. (°C.) | $Me_2AlCPD$ (mM) | tBuCl (mM) | Time (min) | Yield (%) | $Mn \times 10^{-3}$ | Cyclopentadiene content (wt %) |
|---|---|---|---|---|---|---|---|---|---|---|
| 1 | 2.1 | 4.2 | 9.5 | −41 | 0.10 | 0.20 | 52 | 3 | 13.3 | .49 |

Table III-continued

| Run | Isobutylene (ml) | n-pentane (ml) | Chlorobenzene (ml) | Temp. (°C.) | Me₂AlCPD (mM) | tBuCl (mM) | Time (min) | Yield (%) | $\overline{M}_n \times 10^{-3}$ | Cyclopentadiene content (wt %) |
|---|---|---|---|---|---|---|---|---|---|---|
| 2 | 4.2 | 2.1 | " | " | " | " | 34 | 4 | 28.8 | .23 |
| 3 | 6.3 | 0 | " | " | " | " | 16 | 3 | 47.1 | .14 |
| 4 | 3.0 | 0 | 13 | −33 | 0.10 | 1.6 | 52 | 90 | | 1.25 |
| 5 | " | " | " | −27 | " | 0.8 | 45 | 54 | | 0.87 |
| 6 | " | " | " | −20 | " | 0.8 | 30 | 58 | | 0.85 |

Me₂AlCPD was added, followed by tBuCl. Polymerizations were terminated by shortstopping and coagulation with methanol. The polymers were vacuum dried at 30° C. for 72 hrs. Cyclopentadiene content was determined by UV analysis (employed $\lambda_{max}$ and extinction coefficient for tBuCPD) of purified samples (reprecipitated three times from spectro grade n-hexane). Representative results are presented in Table III.

Runs 1, 2 and 3 show the effect of monomer concentration on subsequent cyclopentadiene end group concentration. Thus as the initial monomer concentration increases, the polymer molecular weight increases. Subsequently, the end group concentration decreases, leading to a lower cyclopentadiene content. However, from the $\overline{M}_n$ (from GPC) and cyclopentadiene concentration, it is calculated that approximately 72% of of the polymer chains from polymerizations at −41° C. contain a cyclopentadiene end group.

Runs 4, 5 and 6 show the effect of polymerization temperature on subsequent cyclopentadiene content. Thus the lower temperatures favor termination by alkylation with the cyclopentadiene group, paralleling that observed in the synthesis of tBuCPD.

The polymers prepared in a manner such as that of Example 4 and similar to that of Example 4 can be utilized in a variety of ways. For instance two or more polymer chains containing a terminal cyclopentadiene group can be heated and the cyclopentadiene portions will undergo a Diels-Alder condensation or dimerization and thereby obtain a chain extension.

Polyisobutylene containing terminal cyclopentadiene groups can be reacted with maleic anhydride in a Diels-Alder condensation to give polymers containing norbornene dicarboxylic anhydride end groups. Polymers containing such end groups could be employed in a variety of reactions such as macromer in polyester synthesis or such polymers could be condensed with cellulose via the reaction of the hydroxyl groups of the cellulose with the anhydride group of the polyisobutylene.

Graft polymers may be prepared by reacting the polyisobutylenes containing terminal cyclopentadiene groups with polymers containing pendant cyclopentadiene groups such as those prepared in accordance with this invention to obtain polymers containing polyisobutylene pendant side chains. For instance, a polymer prepared from chlorinated butyl could be reacted in accordance with the present invention, produce polymers containing pendant cyclopentadiene groups and such polymers could be reacted with polyisobutylene containing terminal cyclopentadiene groups thereby forming a graft polymer having polyisobutylene grafted onto a polyisobutylene/isoprene backbone. In addition to these high polymer applications, liquid polyisobutylene containing a terminal cyclopentadienyl group can also be used in adhesives, viscosity index improvers and motor oil additives.

Therefore, one embodiment of this invention are compositions comprising polyisobutylene containing a terminal cyclopentadienyl group of the formula:

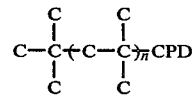

wherein n ranges from about 25 to about 25,000 and CPD is cyclopentadiene. Another set of interesting polymers would be those in which the degree of polymerization indicated by n in the formula above would range from about 90 to about 18,000. Still other interesting polyisobutylene containing terminal cyclopentadienyl groups in which the polyisobutylene degree of polymerization ranges from about 260 to about 2600.

While certain representative embodiments and details have been shown for the purpose of illustrating the invention it will be apparent to those skilled in this art that various changes and modifications may be made therein without departing from the spirit or scope of the invention.

What is claimed is:

1. A method for preparing a polymer containing a cyclopentadiene terminal group which comprises reacting a material selected from the group consisting of isobutylene, styrene and α-methylstyrene with an initiator consisting of tertiary, allylic or benzylic halide of the formula RX, wherein R is selected from the group consisting of alkyl, cycloalkyl, alkenyl, cycloalkenyl, alkaryl or aryl, and X represents chlorine, bromine or iodine, and $R_{x'}Al(CPD)_y$ wherein CPD represents the cyclopentadiene group, R' represents an alkyl, cycloalkyl, alkenyl, cycloalkenyl, alkaryl or aryl group, y equals 1 to 2 and x equals 2 to 1 and the sum of x plus y is equal to 3.

2. A method according to claim 1 in which the $RX/R_{x'}Al(CPD)_y$ mole ratio ranges from 0.1/1 to 5.0/1.

3. A method according to claim 2 in which RX is tertiary butyl chloride and $R_{x'}Al(CPD)_y$ is dimethyl aluminum cyclopentadiene or dimethyl(cyclopentadienyl)aluminum.

4. A method according to claim 3 in which the monomer is isobutylene.

* * * * *